United States Patent [19]

Hirano et al.

[11] Patent Number: 5,448,168
[45] Date of Patent: Sep. 5, 1995

[54] VARIABLE-ORIENTATION MAGNETIC FIELD APPLICATION APPARATUS FOR LOAD APPLICATION MEANS

[75] Inventors: Kazumi Hirano; Takayuki Suzuki, both of Tsukuba, Japan

[73] Assignees: Agency of Industrial Science & Technology; Ministry of International Trade & Industry, both of Tokyo, Japan

[21] Appl. No.: 38,248

[22] Filed: Mar. 29, 1993

[30] Foreign Application Priority Data

Mar. 31, 1992 [JP] Japan ............................ 4-105399

[51] Int. Cl.⁶ .................... G01N 3/00; G01B 7/24; G01R 33/12
[52] U.S. Cl. .................................. 324/209; 73/788; 73/862.69; 324/228; 324/262
[58] Field of Search ............. 324/209, 228, 232, 262, 324/377; 73/779, 788, 821, 826, 862.626, 862.69

[56] References Cited

U.S. PATENT DOCUMENTS

| | | | |
|---|---|---|---|
| 3,375,438 | 3/1968 | Auer | 324/377 X |
| 3,492,566 | 1/1970 | Gross | 324/377 X |
| 3,496,459 | 2/1970 | Foner | 324/377 X |
| 3,609,526 | 9/1971 | Chaberski | 324/377 X |

OTHER PUBLICATIONS

S. Emura et al. Process of Int. Conf. on Stainless Steels Makuhari, Japan 1991.

*Primary Examiner*—Gerhard R. Strecker
*Attorney, Agent, or Firm*—Oblon, Spivak, McClelland, Maier & Neustadt

[57] ABSTRACT

An apparatus for evaluating the mechanical properties of a material has a superconducting magnet that has a plurality of magnet windings arranged side by side in the direction of a longitudinal axis of the magnet. The interior of the magnet is provided with a vertical space and a horizontal space for housing a test specimen in alignment with its longitudinal axis and at right-angles to the longitudinal axis. The apparatus is also provided with a fitting so that the magnet can be attached in an orientation that is in alignment with a longitudinal axis of the vertical space, and can be rotated by 90 degrees in a plane that includes a longitudinal axis of the horizontal space to thereby be oriented in a second direction.

1 Claim, 6 Drawing Sheets

VARIABLE-ORIENTATION MAGNETIC FIELD APPLICATION APPARATUS FOR LOAD APPLICATION MEANS

BACKGROUND OF THE INVENTION

1. Field of the Invention

This invention relates to an apparatus for evaluating the mechanical properties of materials that can evaluate the mechanical properties of a test specimen in magnetic fields of two different orientations.

2. Description of the Prior Art

In superconducting generators, superconducting magnetic energy storage devices, linear motors and other such superconducting device technologies, the importance of the relationship between the mechanical properties and the magnetic field orientation of superconducting materials and structural materials is such that prior evaluation of this relationship is required. However, the difficulty of making an apparatus for evaluating data relating to the mechanical properties of such materials has meant that the amount of such data that has been collected is insufficient.

In a conventional apparatus for evaluating the mechanical properties of a material in a magnetic field, a test specimen is placed in a superconducting magnetic field and subjected to a load while the strength of the material under the load is evaluated. Such apparatuses for evaluating the mechanical properties of a material having a unidirectional magnetic field orientation have already been announced. For example, on page 119 of the proceedings of the 45th meeting on Cryogenics and Superconductivity of the Cryogenic Association held in the spring of 1991, a system arrangement is shown in which a solenoid type magnet in which a relatively high magnetic field can be readily generated is used to apply a load in order to evaluate the properties of a material in a magnetic field oriented in the same direction as that of the direction in which the load is applied.

However, while a solenoid type magnet can be used to evaluate the mechanical properties of a test specimen in a unidirectional magnetic field, the magnetic field orientation cannot be changed. This makes it impossible to evaluate the mechanical properties of a material under different magnetic field orientations, and as such makes it inadequate for evaluating the mechanical properties of materials that are to be used in fields relating to superconduction technology. While for the purpose of evaluating the mechanical properties of a material in different magnetic field orientations a separate superconducting magnet may be provided to generate a magnetic field in a different direction, such an arrangement would require the provision of at least two superconducting magnets, which would thereby increase the size and cost of such an apparatus.

SUMMARY OF THE INVENTION

An object of the present invention is to provide an apparatus for evaluating the mechanical properties of materials in variable magnetic field orientations in which a single superconducting magnet is used to change the orientation of the magnetic field to perform various tests for evaluating mechanical properties such as tensile tests and fracture toughness tests.

In accordance with the present invention, this object is attained by an apparatus for evaluating the mechanical properties of a material, comprising load application means for applying a load to a test specimen, and a split type superconducting magnet for applying a magnetic field to the test specimen under load, wherein the superconducting magnet has a plurality of magnet windings arranged side by side and separated by a prescribed distance which are disposed in the direction of the center line thereof, and the interior of the magnet is provided with a first space for accommodating a test specimen in the direction of said center line, and a second space for accommodating a test specimen at right-angles to the direction of said center line, said magnet comprising a first fixing means for fixing said magnet to the load application means in the orientation of the test specimen accommodated in the first space, and a second fixing means for fixing said magnet to the load application means in the orientation of the test specimen accommodated in the second space.

To test materials in two different magnetic field orientations using this apparatus for evaluating the mechanical properties of materials in a variable magnetic field orientation thus configured, the first fixing means is used to affix the split type magnet vertically to the main unit of the evaluation apparatus. In doing this, the center line of the first space (vertical space) of the magnet is aligned to coincide with the center line of the load application means. In this state, the test specimen is affixed to the load application means so that the center line of the test specimen coincides with the center line of the vertical space, and the test specimen is put under load by the load application means to perform a material test in a vertical magnetic field.

Next, to perform a material test in a magnetic field having an orientation that differs by 90 degrees from the above vertical orientation, the magnet is detached from the load application means, rotated 90 degrees and reaffixed to the load application means by means of the second fixing means, the center line of the horizontal space aligned to coincide with the center line of the load application means. One magnet can thus readily be used to evaluate mechanical properties under two magnetic field orientations, which is economical.

Further features of the invention, its nature and various advantages will be more apparent from the accompanying drawings and following detailed description of the invention.

DESCRIPTION OF THE PREFERRED EMBODIMENT

Figure 5:
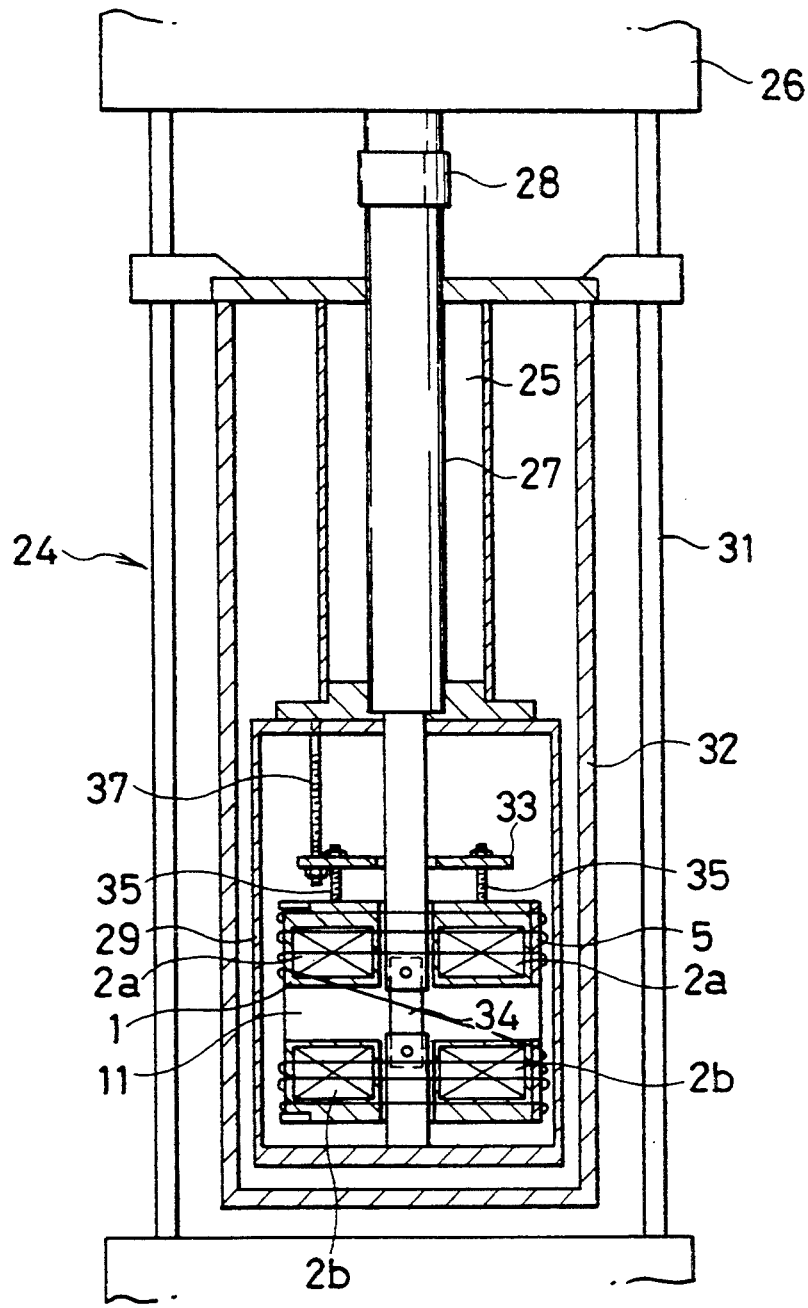
FIG. 5 is a view illustrating the apparatus for evaluating the mechanical properties of materials with the magnetic field generator attached vertically thereto.
Figure 6:
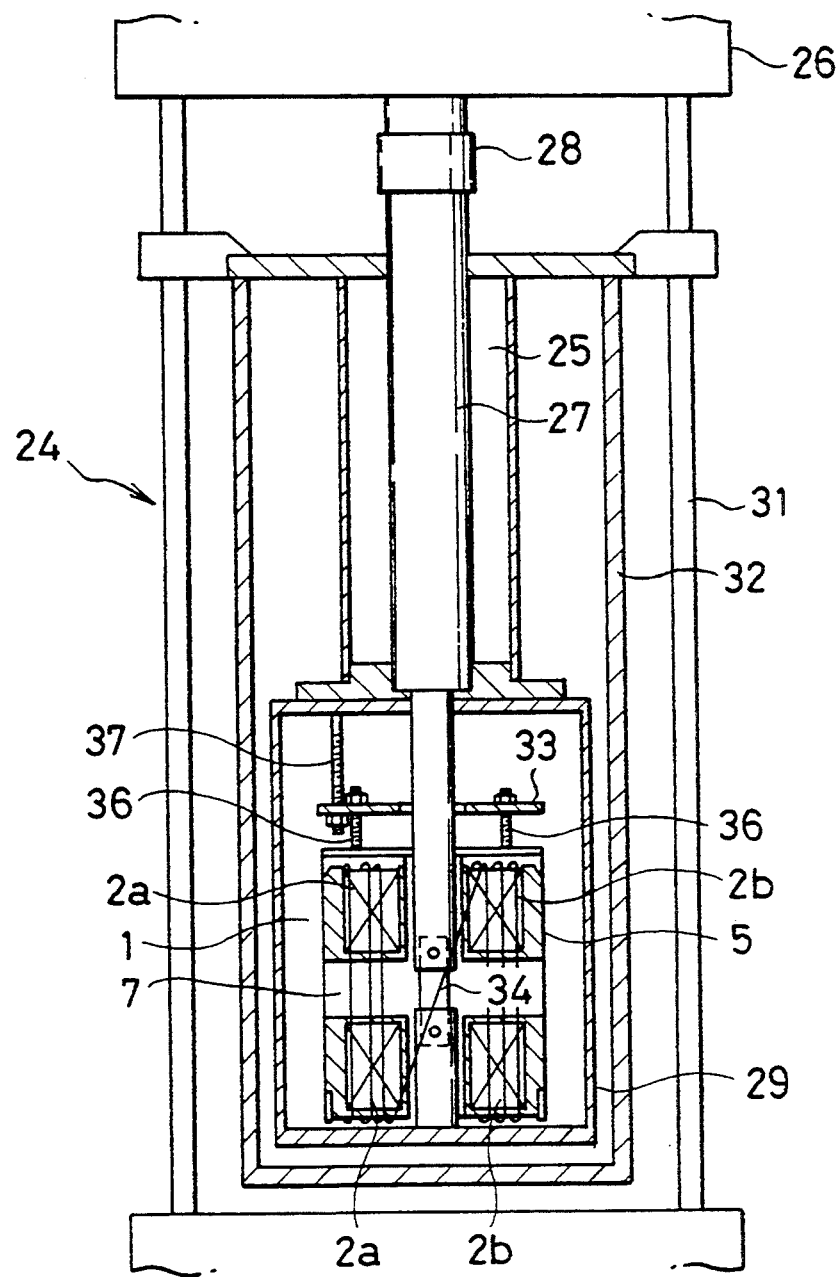
FIG. 6 shows the same apparatus with the magnetic field generator attached horizontally thereto.

Details of the present invention will now be described with reference to the illustrated embodiments. As shown by FIGS. 5 and 6, the apparatus 24 for evaluating the mechanical properties of materials in a variable magnetic field orientation comprises a load application means 25 for applying a load to a test specimen 34, and a magnetic field generator 1 that is provided below the load application means 25 and is for applying a magnetic field to the test specimen 34 while the test specimen 34 is being subjected to the load.

Figure 1:
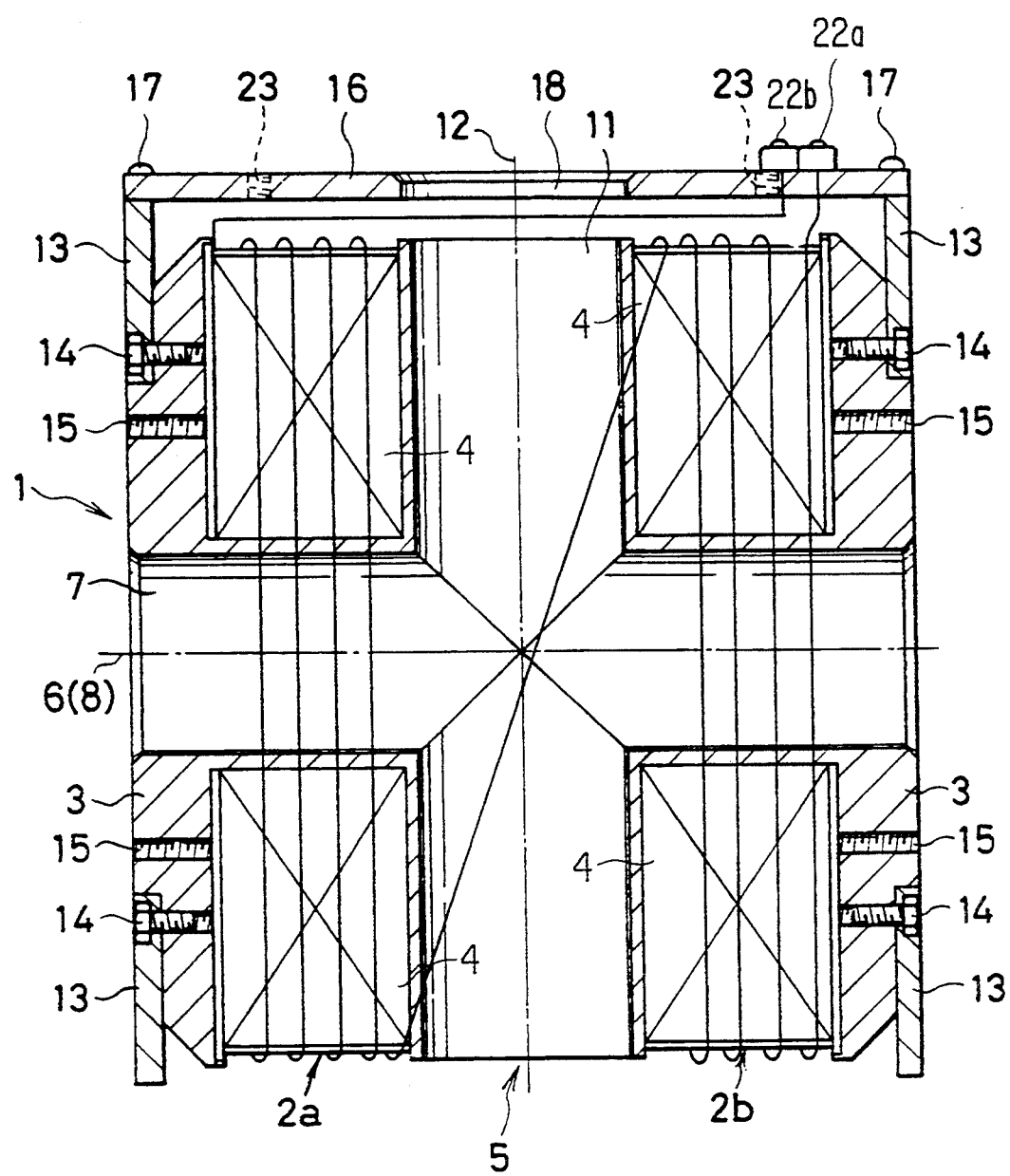
FIG. 1 is a frontal cross-sectional view of an embodiment of the magnetic field generator of the apparatus for evaluating the mechanical properties of materials according to the present invention.
Figure 2:
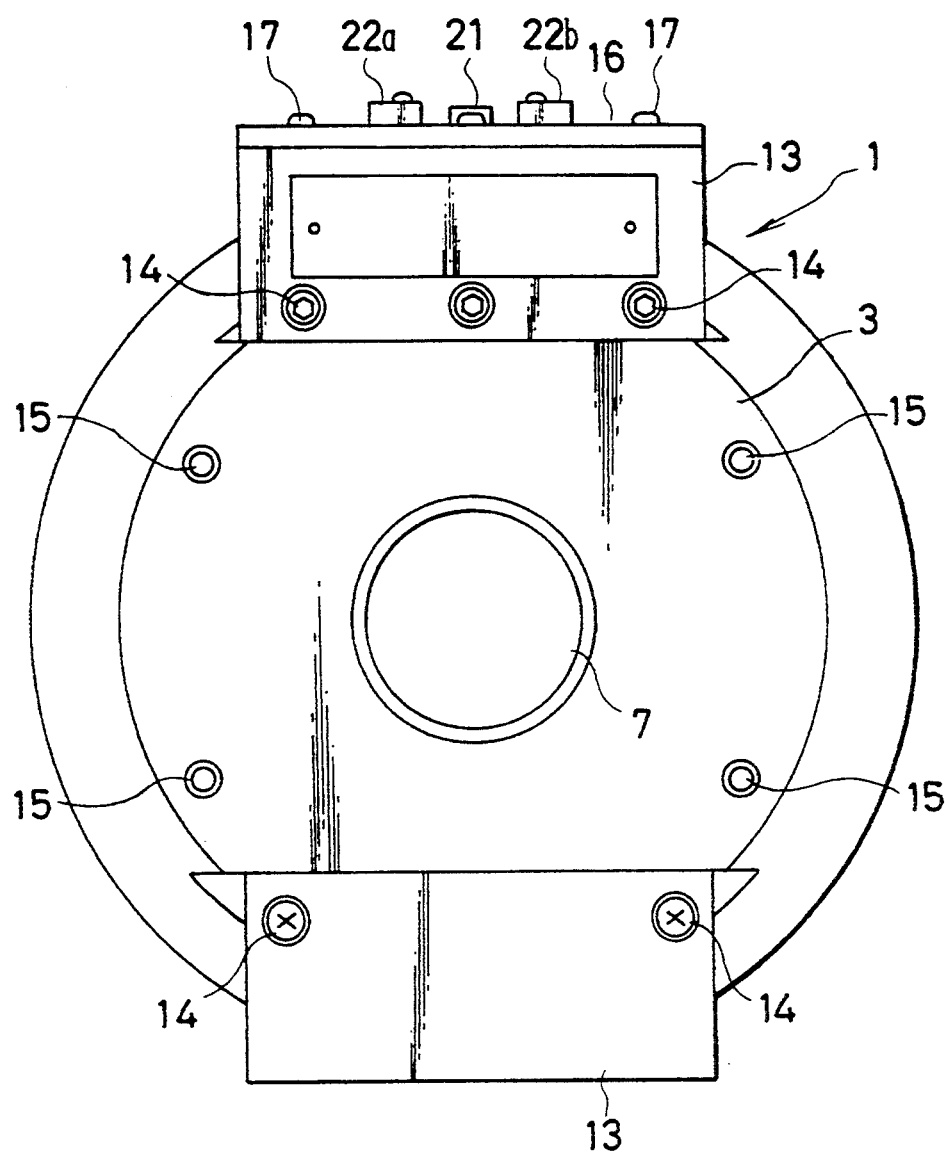
FIG. 2 is a side view of the magnetic field generator of FIG. 1.
Figure 3:
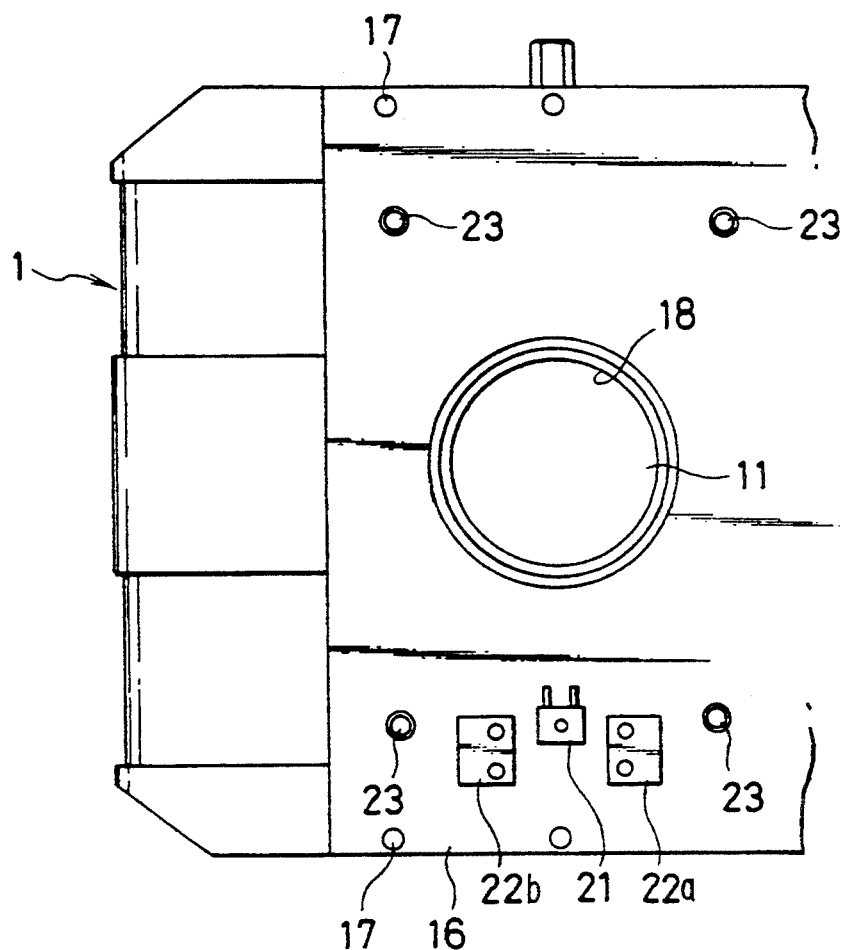
FIG. 3 is a plan view of the magnetic field generator of FIG. 1.
Figure 4:
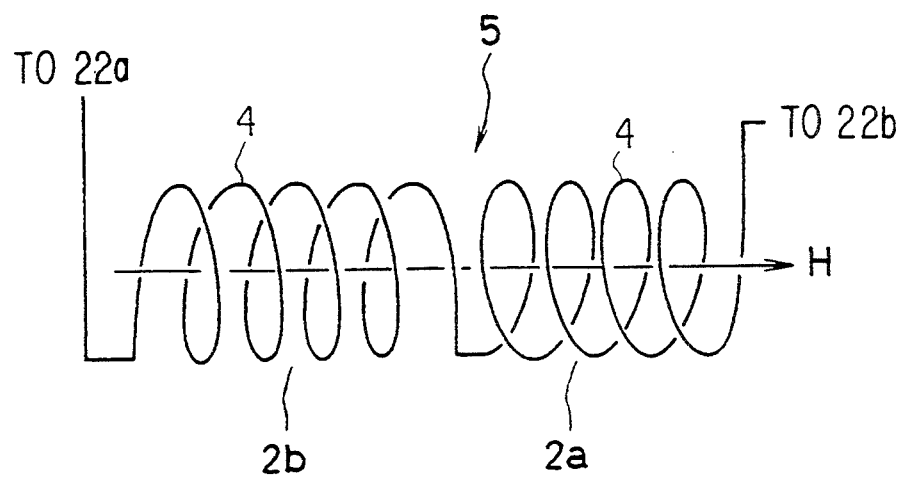
FIG. 4 is a diagram illustrating the connections of the split type superconducting magnet winding.

As shown in FIGS. 1–3, the magnetic field generator 1 is provided with a first magnet 2a and a second magnet 2b. The first magnet 2a and second magnet 2b are each provided with a magnet winding 4 on a bobbin 3. The wiring arrangement of each of the windings 4 is shown in FIG. 4, whereby a split type superconducting magnet 5 is constituted by the first magnet 2a and second magnet 2b.

The first magnet 2a and second magnet 2b are arranged adjacent to each other along the direction of the center line 6 of the split type superconducting magnet 5, with a space in between. A vertical space 7 is formed along the direction of the center line 6 of the split type superconducting magnet 5. This vertical space 7 is in the form of an opening having a circular cross-section in which to arrange a test specimen, and the center line 8 of the space coincides with the center line 6 of the split type superconducting magnet 5. A horizontal space 11 is formed between the first magnet 2a and second magnet 2b that has a center line 12 that is at right-angles to the center line 6.

Figure 7:
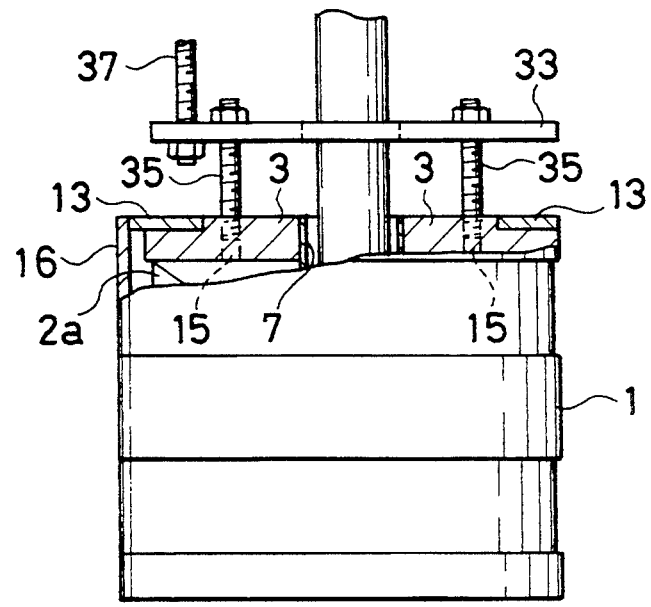
FIG. 7 is a view illustrating the magnetic field generator in the vertical state.

This horizontal space 11 is in the form of an opening having a circular cross-section in which to accommodate a test specimen, and the center line 12 thereof forms an angle of 90 degrees with the center line 8 of the vertical space 7. Fixing screws 14 are used to affix a side plate 13 to the bobbins 3 at each of the end portions in the direction of the center line 6 of the split type superconducting magnet 5. Provided on each side of the bobbins are four screw-holes 15 for screws 35 (FIG. 7) that depend vertically. These screws 35 are used to affix the split type superconducting magnet 5 to the apparatus 24 (FIG. 5) so that the center line 8 of vertical space 7 is lined up with the center line of the load application means 25.

Figure 8:
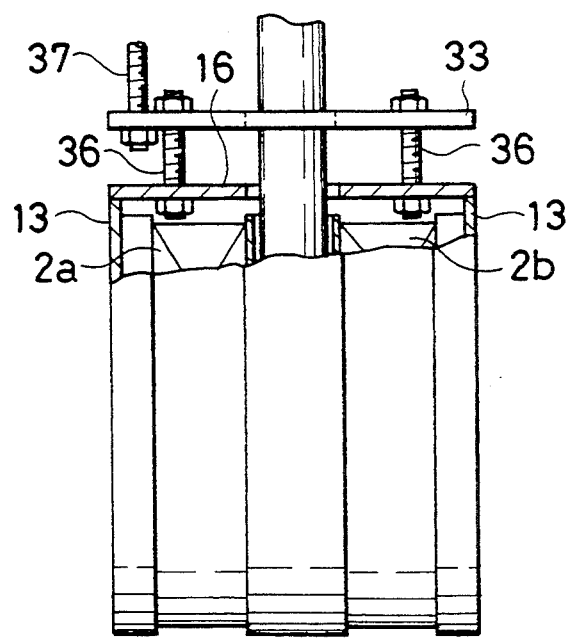
FIG. 8 is a view illustrating the magnetic field generator in the horizontal state.

As shown in FIGS. 1–3, the end portion in the direction that is at right-angles to the direction of the center line 8 of the split type superconducting magnet 5, a terminal plate 16 is affixed to the side plate 13 by fixing screws 17. Formed in the terminal plate 16 is a through-hole 18 that is concentric with the horizontal space 11. The terminal plate 16 is provided with a measurement terminal 21 and electric current terminals 22a and 22b. Provided around the hole 18 are four screw-holes 23 for screws 36 (FIG. 8) that depend horizontally. These screws 36 are used to affix the split type superconducting magnet 5 to the apparatus 24 (FIG. 6) so that the center line 12 of the horizontal space 11 is lined up with the center line of the load application means 25.

As shown in FIGS. 5 and 6, the load application means 25 has a load cell 28 attached to a pull-rod 27 that extends from a cross-head 26. Attached to the lower edge of the cross-head 26 is a frame 31 which supports a cryostat 32. The interior of the cryostat 32 is filled with a cryogen such as liquid helium or the like for cooling the test specimen 34 in the magnetic field generator 1 within a housing 29. A bracket member 37 extends vertically downward from the top of the housing 29. Affixed horizontally at the end of the bracket member 37 is a flange 33 from which the magnet is suspended. This flange 33 is provided with a hole through which the test specimen 34 is inserted.

Testing of the test specimen 34 in two magnetic field orientations by means of the material evaluation apparatus 24 thus configured will now be described. First, to perform testing with the central axis of the test specimen 34 in alignment with the magnetic field orientation, the test specimen 34 is affixed to the pull-rod 27 so the center line of the load application means 25 and the longitudinal axis of the test specimen 34 are in alignment, and with the test specimen 34 inserted in the vertical space 7 of the split type superconducting magnet 5, the screws 35 are used to suspend the split type superconducting magnet 5 inside the housing 29 of the load application means 25, as illustrated by FIG. 5. More specifically, with reference to FIG. 7, one end of each of the four screws 35 is screwed into one of the corresponding holes 15 provided on the side of the bobbins 3, and each of the other ends is affixed to the flange 33 with a nut to thereby suspend the split type superconducting magnet 5.

In this state, the cryostat 32 is then charged with the cryogen to maintain the test specimen 34 at a cryogenic temperature while the load application means 25 applies a load to the test specimen 34 to evaluate the mechanical properties of the material test specimen. In this case this evaluation is performed with the test specimen 34 arranged so that the direction in which the load is applied is the same as the orientation of the magnetic field.

Next, to change the magnetic field orientation in order to evaluate the mechanical properties of the test specimen 34 with the magnetic field oriented at right-angles to the longitudinal axis of the test specimen 34, the magnet 5 is detached and rotated 90 degrees, bringing the center line 12 of the horizontal space 11 of the magnet 5 into alignment with the central axis of the load application means 25, and with the test specimen 34 still inserted in the horizontal space 11, the screws 36 are used to suspend the magnet 5 inside the housing of the load application means 25 as shown in FIG. 6. That is, with reference to FIG. 8, one end of each of the four screws 36 is screwed into one of the corresponding holes 23 provided in the terminal plate 16, or held in place by a nut, and each of the other ends is affixed to the flange 33 by means of a nut to thereby suspend the magnet 5 in the housing. The result is that the magnetic field orientation of the magnet 5 forms a right-angle with the longitudinal axis of the test specimen 34, and the test specimen maintained at a cryogenic temperature is subjected to a load to evaluate its mechanical properties with the direction of the load at right-angles to the magnetic field orientation.

The foregoing description was made with reference to a method involving the use of screws 35 and 36 to suspend the magnet 5 in the housing 29 by affixing it to the flange 33. However, it is to be understood that the fixing method is not limited thereto, and that any other suitable fixing means may be used that accomplishes the attachment so that the alignment of the central axis of the load application means coincides with the alignment of the center line of the vertical space 7 or horizontal space 11 of the magnet 5.

Thus, in accordance with the present invention, a hole is provided for housing a test specimen aligned with the magnetic field orientation of a superconducting magnet and at right-angles thereto, and by attaching the magnet to the load application means in a different orientation, a single magnet can readily be used to perform various tests such as tensile tests and fracture toughness tests to evaluate the mechanical properties in two orthogonal magnetic field orientations, which is economical.

What is claimed is:

1. An apparatus for evaluating mechanical properties of a material, comprising:

load application means for applying a load to a test specimen;

a structure having first and second hollow, open-ended tubes perpendicularly intersecting one another at centers thereof, said first tube defining a first internal space therein and said second tube defining a second internal space therein;

superconducting magnet means for applying a magnetic field to said test specimen under load, said superconducting magnet means comprising a pair of magnet windings, a first of which is wound around said first tube on one side of the intersection with said second tube, and a second of which is wound around said first tube on the other side of said intersection with said second tube, said pair of magnet windings being connected in series;

first fixing means for fixing said superconducting magnet means to said load application means while said test specimen is within said first internal space such that said magnetic field is generated and applied to said test specimen in a same direction in which a load is applied to said test specimen via said load application means; and second fixing means for fixing said superconducting magnet means to said load application means while said test specimen is within said second internal space such that said magnetic field is generated and applied to said test specimen in a direction which is perpendicular to a direction in which a load is applied to said test specimen via said load application means.

* * * * *